| United States Patent [19] | [11] 4,286,592 |
|---|---|
| Chandrasekaran | [45] Sep. 1, 1981 |

[54] THERAPEUTIC SYSTEM FOR ADMINISTERING DRUGS TO THE SKIN

[75] Inventor: Santosh K. Chandrasekaran, Palo Alto, Calif.

[73] Assignee: ALZA Corporation, Palo Alto, Calif.

[21] Appl. No.: 117,846

[22] Filed: Feb. 4, 1980

[51] Int. Cl.³ .............................................. A61M 7/00
[52] U.S. Cl. .................................... 128/260; 128/156
[58] Field of Search ............................... 128/155–156, 128/270, 260

[56] References Cited

U.S. PATENT DOCUMENTS

| 3,598,122 | 8/1971 | Zaffaroni | 128/268 |
|---|---|---|---|
| 3,797,494 | 3/1974 | Zaffaroni | 128/268 |
| 4,060,084 | 11/1977 | Chandrasekaran | 128/260 |
| 4,230,105 | 10/1980 | Harwood | 128/156 |
| 4,237,888 | 12/1980 | Roseman et al. | 128/270 |

*Primary Examiner*—C. Fred Rosenbaum
*Attorney, Agent, or Firm*—Paul L. Sabatine; Edward L. Mandell

[57] ABSTRACT

A bandage for administering drugs to the skin that consists of an impermeable backing layer, a drug reservoir layer composed of drug and a carrier, and a contact adhesive layer by which the bandage is adhered to the skin. The contact adhesive layer controls the rate at which drug is administered and maintains that rate at an approximately constant level by virtue of there being a particular correlation between the solubility of the drug in the carrier and in the contact adhesive, the diffusion coefficient of the drug in the carrier and in the contact adhesive, the concentration of drug in the reservoir, and the thickness of the contact adhesive layer.

5 Claims, 3 Drawing Figures

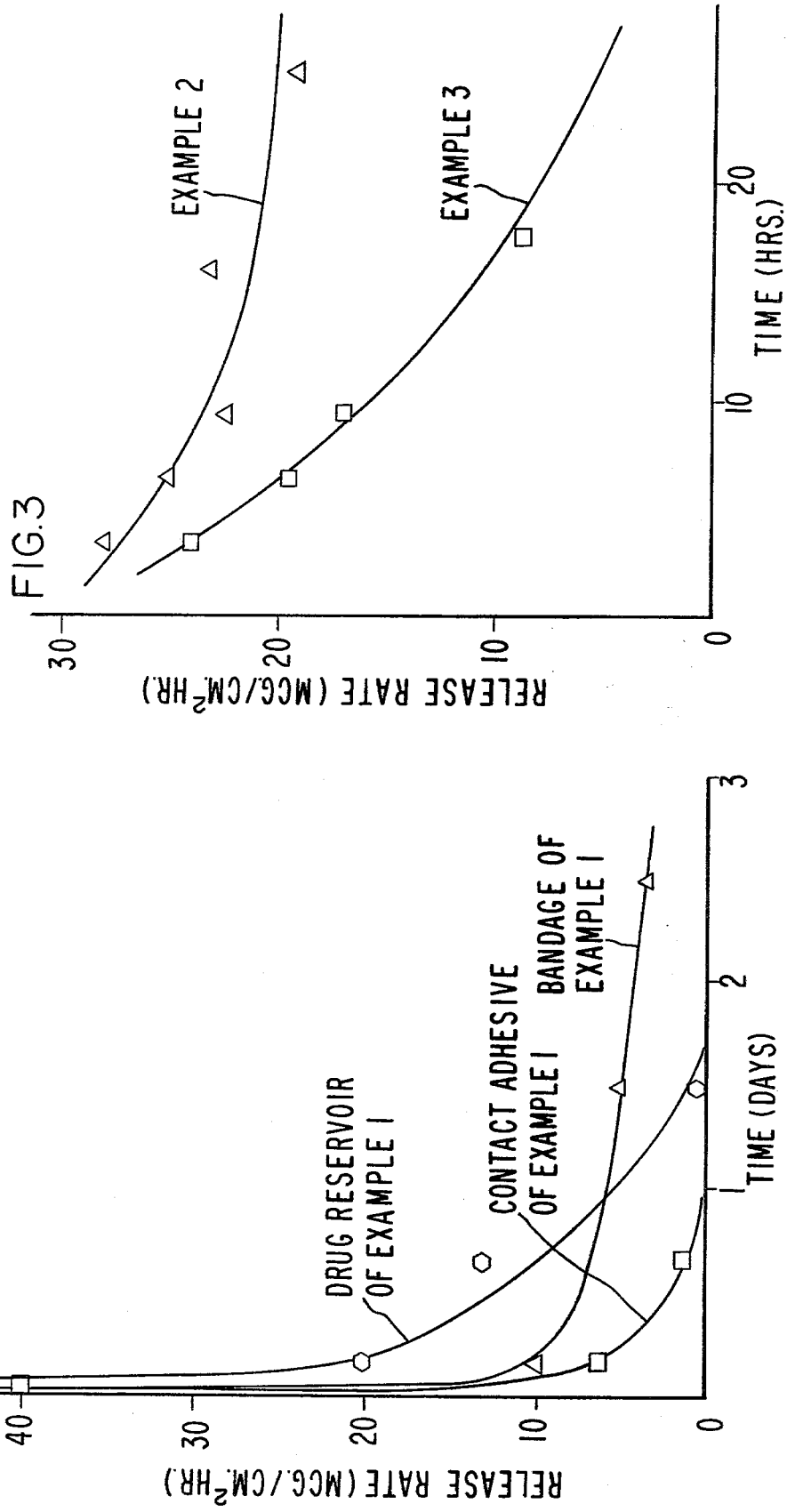

THERAPEUTIC SYSTEM FOR ADMINISTERING DRUGS TO THE SKIN

FIELD OF THE INVENTION

This invention relates to therapeutic systems in the form of bandages that administer drugs to the skin at an approximately constant rate over a substantial portion of the administration period.

DESCRIPTION OF THE PRIOR ART

Bandages that administer drugs to the skin or mucosa have been known for some time. U.S. Pat. No. 3,249,109 describes a two layer topical dressing that consists of an adhesive base layer made of hydrated gelatin and drug, and a fabric backing layer. Such bandages typically release drug at either an unpredictable or inconstant rate.

In the early 1970s patents relating to bandages that release drug at a substantially constant rate began to appear. U.S. Pat. No. 3,598,122 describes a multilayer bandage comprising a backing layer, a drug reservoir layer, and a contact adhesive layer by which the bandage is stuck to the skin or mucosa. The drug reservoir may consist of a core of either neat drug or drug mixed with a drug permeable carrier and a wall that surrounds the core and is made of a drug release rate controlling material. The rate of drug release depends on the rate at which drug diffuses through the wall. U.S. Pat. No. 3,797,494 describes another type of substantially constant release bandage. The '494 bandage is a sandwich-type laminate having a backing layer, a drug reservoir layer made from a drug-carrier mixture, a drug release rate controlling microporous membrane layer, and a contact adhesive layer. The rate of drug release from the '494 bandage depends on the rate at which drug diffuses through the microporous membrane. In the bandages of both '122 and '494 the contact adhesive layer plays a passive, insignificant role with respect to drug release rate; that is, the drug that passes through the wall/membrane migrates quickly through the contact adhesive layer to the skin. Compared to the simple two layer bandage of the '109 patent these substantially constant release bandages function well. They are, however, more complex and hence costlier than the more simple bandages.

DISCLOSURE OF THE INVENTION

The invention resides in the discovery that an approximately constant release of drug may be achieved from a bandage that is a relatively simple laminate of a backing layer, a drug reservoir layer, and a contact adhesive layer and which does not involve the drug release rate controlling wall or microporous membrane of the above-described patents. This unexpected achievement rests on there being a particular correlation between the solubility of the drug in the contact adhesive composition and in the carrier of the drug reservoir, the diffusion coefficient of the drug in the contact adhesive composition and in the carrier of the drug reservoir, the concentration of drug in the drug reservoir, and the thickness of the contact adhesive layer.

Specifically, the invention is a therapeutic system, in the form of a bandage, for administering a drug to the skin for a predetermined time period consisting essentially of:

(a) a backing lamina that is substantially impermeable to the drug, one face of which forms the top of the bandage;

(b) a drug reservoir lamina adjacent the opposite face of the backing lamina comprising the drug dispersed in a carrier that is permeable to the drug; and (c) a contact adhesive lamina adjacent and below the drug reservoir lamina comprising a contact adhesive composition that is permeable to the drug, wherein the following conditions are met over a substantial portion of said time period (i) the concentration of the drug in the contact adhesive lamina, $C_{CA}$ mg/cm$^3$, is not greater than the solubility of the drug in the contact adhesive composition, $C_{SCA}$ mg/cm$^3$, and (ii) the ratio $$\frac{D_{CA} \cdot C_{SCA}}{l_{CA} \cdot \left( \frac{D_{DR} \cdot C_{DR} \cdot C_{SDR}}{t} \right)^{\frac{1}{2}}}$$

is in the range of about 0.01 and about 0.7, wherein $D_{CA}$ is the diffusion coefficient of the drug in the contact adhesive composition in cm$^2$/hr, $l_{CA}$ is the thickness of the contact adhesive lamina in cm, $D_{DR}$ is the diffusion coefficient of the drug in the carrier in cm$^2$/hr, $C_{DR}$ is the concentration of drug in the drug reservoir in mg/cm$^3$, $C_{SDR}$ is the solubility of the drug in the carrier in mg/cm$^3$, and t is any time during said time period in hr.

The term "substantial" as applied to said time period is intended to mean at least 50%. Typically the conditions will prevail over at least 75% of the time period. The maintenance of such conditions will typically result in the release rate declining less than 30% over the time period.

BRIEF DESCRIPTION OF THE DRAWINGS

In the drawings:

FIG. 1, which is not to scale, is a sectional view of the invention bandage;

FIG. 2 is a graph of scopolamine release rate versus time for the bandage of Example 1 and the components thereof; and FIG. 3 is a graph of nitroglycerin release rate versus time for the bandages of Examples 2 and 3.

DESCRIPTION OF EMBODIMENTS OF THE INVENTION

FIG. 1 illustrates the basic structure of the bandage, generally designated 10, before it is applied to the skin. The components of bandage 10 are, from the top: an impermeable backing layer 11, a drug reservoir layer 12 composed of a drug 13 dispersed in a carrier 14, a contact adhesive layer 15, and an impermeable strippable coating or release liner layer 16. Layer 16 is removed to expose layer 15 before the bandage is applied to the skin. Depending on the particular drug, carrier, and adhesive composition involved it may be necessary or desirable to enclose the sides of the bandage 10 with an impermeable coating or otherwise seal the sides to prevent drug, carrier, and/or adhesive from evaporating, bleeding, exuding, leaking or otherwise exiting from the bandage via its sides.

Backing layer 11 prevents drug from being released via the top surface of reservoir layer 12. It also serves as a protective layer or cover for the bandage when it is in place on the skin or mucosa. As such, it must be impermeable to the drug, water, and the carrier. Materials for making such backing members are disclosed in the art, for instance in U.S. Pat. No. 3,598,122 at column 5, lines 56 to 71, which disclosure is incorporated herein by reference.

Drug reservoir 12 is composed of a mixture of a carrier and the drug. In most instances the drug will initially be present greatly in excess of its solubility in the carrier material. Thus, the drug is present in the reservoir in both dissolved and undissolved form. The drug content of the reservoir should be kept below the concentration at which the carrier ceases to be a continuous phase and there is significant particle-to-particle contact between dispersed drug particles. Typically the maximum drug content that can be achieved without encountering such conditions is about 35% drug by volume in the reservoir. As indicated previously, the carrier is permeable to the drug. In this regard, the solubility of the drug in the carrier will usually be in the range of about 0.1 mg/cm$^3$ to about 100 mg/cm$^3$ and the diffusion coefficient of drug in the carrier will normally be in the range of about $1 \times 10^{-11}$ to about $1 \times 10^{-7}$ cm$^2$/sec. Preferably the drug reservoir mixture is in the form of a cohesive semisolid, such as a gel, that adheres strongly to the backing layer and contact adhesive layer. Otherwise, means for confining the reservoir and providing structural integrity for the system must be included. Examples of such means are side walls, overlays, and edge sealing. The particular carrier to be used will depend in large part upon the particular drug involved. Silicone-based carriers and carriers made from mixtures of mineral oil and polyisobutenes may be used with many drugs. The patents referred to in the Description of Prior Art above disclose examples of other carriers that may be used.

The contact adhesive layer 15 plays the principal role in controlling the rate at which drug is released from bandage 10. It, too, is permeable to the drug. The solubility of the drug in the composition from which the layer is made will normally be in the same range as for the carrier, namely 0.1 to 100 mg/cm$^3$. Likewise the diffusion coefficient of the drug in the contact adhesive composition will usually be in the range of $1 \times 10^{-11}$ to $1 \times 10^{-7}$ cm$^2$/sec. As indicated above, the concentration of drug in the contact adhesive layer is less than the solubility of the drug in the contact adhesive composition over at least a substantial portion of the time period over which the drug is to be administered. If no drug is incorporated into the contact adhesive layer before the bandage is attached to the skin, that condition will prevail over the entire time period. On the other hand, if drug is incorporated into the contact adhesive beforehand so that the actual concentration exceeds the solubility, that condition will prevail only after an initial portion of the time period during which the drug is depleted from excess down to saturation and below. Such incorporation of drug into the layer beforehand is made if it is necessary or desirable to administer an initial surge or pulse of drug. However, as indicated the duration of this surge or pulse will be short relative to the total administration period.

Depending on the drug involved and the desired time period over which the drug is to be administered, it may be possible to employ the same material as both the carrier and the contact adhesive composition. When this is done, $D_{CA}$ and $D_{DR}$ will be equal and $C_{SCA}$ and $C_{SDR}$ will be equal and the above ratio may be simplified. Under such circumstances, $l_{CA}$ and $C_{DR}$ become the parameters that may be varied to make a bandage that conforms to the invention. In this regard, the maximum $C_{DR}$ that can be employed is described above. While there is no theoretical minimum or maximum for $l_{CA}$, this parameter will, for practical purposes usually be in the range of 50 microns to 2 mm.

In the invention bandages the ratio $$\frac{D_{CA} \cdot C_{SCA}}{l_{CA} \cdot \left(\frac{D_{DR} \cdot C_{DR} \cdot C_{SDR}}{t}\right)^{\frac{1}{2}}}$$

is in the range of about 0.01 and about 0.7 over a substantial portion of the time period during which the drug is administered. Preferably it will be maintained over the entire period. In this regard, for most therapies the administration period (per bandage) will be in the range of 24 hr and one week.

The following examples further illustrate the invention. They are not intended to limit the invention in any way. Unless indicated otherwise proportions are by weight.

EXAMPLE 1

A. A bandage for administering scopolamine transdermally for approximately 72 hr, such as might be used to inhibit nausea or vertigo, was made as follows. A solution of 1.5 parts high molecular weight polyisobutene (1,200,000 viscosity average molecular weight), 1.9 parts low molecular weight polyisobutene (35,000 viscosity average molecular weight), 3.0 parts mineral oil (10 cp at 25° C.), 0.8 parts scopolamine, and 41 parts chloroform was solvent cast onto a 0.07 mm thick backing film of aluminized polyester. The resulting layer of polyisobutene, mineral oil, and scopolamine was 0.04 mm thick. That layer constituted the drug reservoir of the bandage, with $D_{DR}$ being $2 \times 10^{-8}$ cm$^2$/sec, $C_{SDR}$ being 1 mg/cm$^3$, and $C_{DR}$ being 133.1 mg/cm$^3$. The same mixture of mineral oil and high and low molecular weight polyisobutenes was blended with 0.13 parts of scopolamine and the blend was solvent cast onto a 0.08 mm thick strippable coating layer made of siliconized polyester. The resulting solvent cast layer was 85.3 microns thick ($l_{CA}$). It constituted the contact adhesive layer of the bandage, with $D_{CA}$ being $2 \times 10^{-8}$ cm$^2$/sec, $C_{SDR}$ being 1 mg/cm$^3$, and $C_{CA}$ being 21.82 mg/cm$^3$. The two laminates were then laminated together with the drug reservoir facing the contact adhesive.

B. In vitro release rate tests using standard techniques were carried out on the bandage described in A above. For comparison purposes identical tests were carried out on the drug reservoir alone and the contact adhesive alone. The results of these tests are reported graphically in FIG. 2.

$C_{CA}$ was equal to or less than $C_{SCA}$ after about 10 hr. The above mentioned ratio ranged between about 0.4 and about 0.7 over the period t=24 hr to t=72 hr.

As depicted in FIG. 2 during the first 12 hr the bandage released scopolamine at relatively high rates. This was caused primarily by the initial inclusion of scopolamine in the contact adhesive ($C_{CA}$ at t=0 was about 22 times $C_{SCA}$). Thereafter the release rate leveled off at about 4-6 mcg/cm$^2$ hr. The comparison tests on the drug reservoir alone and the contact adhesive alone clearly show that the release rate of the entire bandage is not related to the sum of the release rates that occur from the components taken by themselves. Note especially that after about 1 day the contact adhesive was exhausted of scopolamine and after about 1½ days the drug reservoir was depleted of scopolamine.

EXAMPLE 2

A. A bandage for administering nitroglycerin transdermally for approximately 24 hr, such as might be used to treat angina, was made as follows. A blend of 67 parts silicone fluid (100,000 cs) and 33 parts of nitroglycerin on lactose (1:10 by weight) was cast onto a 0.07 mm thick backing film of aluminized polyester. The resulting layer of that blend was 0.25 mm thick and it constituted the drug reservoir of the bandage, with $D_{DR}$ being $4 \times 10^{-6}$ cm$^2$/sec, $C_{DR}$ being 33 mg/cm$^3$, and $C_{SDR}$ being 2 mg/cm$^3$. A solution of ethylene/vinylacetate copolymer (9% vinylacetate) in methylene chloride was solvent cast onto a 0.08 mm thick strippable coating layer made of siliconized polyester. The resulting layer of copolymer was 100 microns thick ($l_{CA}$) and constituted the contact adhesive layer of the bandage, with $D_{CA}$ being $7 \times 10^{-9}$ cm$^2$/sec and $C_{SCA}$ being 6 mg/cm$^3$. The two laminates were then laminated together with the drug reservoir facing the contact adhesive.

B. In vitro release rate tests using standard techniques were carried out on the bandage of A above. The results of those tests are reported graphically in FIG. 3 with the data points being designated by triangles. The above mentioned ratio ranged between about 0.03 and 0.08 over the period t=3 to t=30 hr. As shown, the release rate of drug declined slightly over the period but more closely approximated zero order release than first order release.

EXAMPLE 3

A. For comparison purposes a bandage for administering nitroglycerin transdermally for approximately 24 hr was made that did not meet the criteria of the invention. The comparison bandage was made as in Example 2 except that the carrier of the drug reservoir was petrolatum USP rather than silicone fluid, and the contact adhesive layer was 150 microns thick and was made of an ethylene/vinylacetate copolymer containing 18% vinylacetate. $C_{DR}$ was 20 mg/cm$^3$, $C_{SDR}$ was 1.2 mg/cm$^3$, and $D_{DR}$ was $9 \times 10^{-9}$ cm$^2$/sec.

B. In vitro release rate tests on the bandage of A were carried out as in Example 2. The results of these tests are also reported in FIG. 3, with the data points being represented by squares. The above mentioned ratio ranged between about 5.8 and 17 over the period t=3 to t=30 hr. As shown, release rate declined drastically relative to the bandage of Example 2, with release rate closely approximating first order release.

Modifications of the above described bandage that are obvious to those of skill in the pharmaceutical art are intended to be within the scope of the following claims.

I claim:

1. A bandage for administering a drug to the skin or mucosa for a predetermined time period, with t representing a time, in hours, in said time period, consisting essentially of a sandwich type laminate of:
   (a) a backing lamina that is substantially impermeable to the drug, one face of which forms the top of the bandage;
   (b) a drug reservoir lamina adjacent the opposite face of the backing lamina comprising the drug dispersed in a carrier that is permeable to the drug, with the solubility of the drug in the carrier being $C_{SDR}$ mg/cm$^3$, the diffusion coefficient of drug in the carrier being $D_{DR}$ cm$^2$/hr, and the concentration of drug in the drug reservoir being $C_{DR}$ mg/cm$^3$; and
   (c) a contact adhesive lamina adjacent and below the drug reservoir lamina comprising a contact adhesive composition that is permeable to the drug, with the thickness of the contact adhesive lamina being $l_{CA}$ cm, the solubility of the drug in the contact adhesive composition being $C_{SCA}$ mg/cm$^3$, the diffusion coefficient of drug in the contact adhesive composition being $D_{CA}$ cm$^2$/hr, and the concentration of drug in the contact adhesive composition being $C_{CA}$ mg/cm$^3$, wherein over at least a substantial portion of said time period
   (i) $C_{CA}$ is not greater than $C_{SCA}$, and
   (ii) the ratio $$\frac{D_{CA} \cdot C_{SCA}}{l_{CA} \cdot \left( \frac{D_{DR} \cdot C_{DR} \cdot C_{SDR}}{t} \right)^{\frac{1}{2}}}$$

is in the range of about 0.01 to about 0.7.

2. The bandage of claim 1 wherein the substantial portion of the time period is at least 50% of the time period.

3. The bandage of claim 1 wherein the drug constitutes less than 35% of volume of the reservoir.

4. The bandage of claim 1 wherein
$C_{SDR}$ is in the range of 0.1 and 100 mg cm$^3$,
$C_{SCA}$ is in the range of 0.1 and 100 mg cm$^3$,
$D_{DR}$ is in the range of $1 \times 10^{-11}$ and $1 \times 10^{-7}$ cm$^2$/sec,
$D_{CA}$ is in the range of $1 \times 10^{-11}$ and $1 \times 10^{-7}$ cm$^2$/sec, and $l_{CA}$ is in the range of 50 microns and 2 mm.

5. The bandage of claim 4 wherein the carrier comprises silicone or a mixture of polyisobutene and mineral oil.

* * * * *